US011869188B1

(12) United States Patent
Levy et al.

(10) Patent No.: US 11,869,188 B1
(45) Date of Patent: Jan. 9, 2024

(54) SYSTEMS AND METHODS FOR IMPROVING DETECTION OF FETAL CONGENITAL HEART DEFECTS

(71) Applicant: BrightHeart SAS, Paris (FR)

(72) Inventors: Marilyne Levy, Paris (FR); Bertrand Stos, Le Plessis Robinson (FR); Cécile Dupont, Paris (FR)

(73) Assignee: BrightHeart SAS, Paris (FR)

( * ) Notice: Subject to any disclaimer, the term of this patent is extended or adjusted under 35 U.S.C. 154(b) by 0 days.

(21) Appl. No.: 18/183,937

(22) Filed: Mar. 14, 2023

(30) Foreign Application Priority Data

Feb. 22, 2023 (EP) ..................................... 23305235

(51) Int. Cl.
*G06T 7/00* (2017.01)
*A61B 8/00* (2006.01)

(52) U.S. Cl.
CPC ............ *G06T 7/0012* (2013.01); *A61B 8/463* (2013.01); *G06T 2207/10016* (2013.01); *G06T 2207/10132* (2013.01); *G06T 2207/20081* (2013.01); *G06T 2207/30044* (2013.01); *G06T 2207/30048* (2013.01); *G06T 2210/12* (2013.01)

(58) Field of Classification Search
CPC ......... G06T 7/0012; G06T 2207/10016; G06T 2207/10132; G06T 2207/20081; G06T 2207/30044; G06T 2207/30048; G06T 2210/12; A61B 8/463
USPC .......................................................... 382/131
See application file for complete search history.

(56) References Cited

U.S. PATENT DOCUMENTS

| 7,672,491 B2 | 3/2010 | Krishnan et al. |
| 11,478,222 B2 | 10/2022 | Shiran et al. |
| 11,488,298 B2 | 11/2022 | Annangi et al. |
| 11,517,290 B2 | 12/2022 | Aase et al. |

(Continued)

FOREIGN PATENT DOCUMENTS

EP 3964136 A1 3/2022

OTHER PUBLICATIONS

Activity recognition, Wikipedia The Free Encyclopedia, retrieved from the internet URL: https://en.wikipedia.org/wiki/Activity_recognition, 12 pages (2018).

(Continued)

*Primary Examiner* — Van D Huynh
(74) *Attorney, Agent, or Firm* — Eversheds Sutherland (US) LLP; Nicola A. Pisano; Robert D. Ward

(57) ABSTRACT

Systems and methods are provided for aiding the detection and diagnosis of critical heart defects during fetal ultrasound examinations, in which motion video clips are analyzed with machine learning algorithms to identify and select within the motion video clips image frames that correspond to standard views recommended by fetal ultrasound guidelines, and selected image frames are analyzed with machine learning algorithms to detecting and identify morphological abnormalities indicative of critical CHDs associated with the standard views. The results of the analyses are presented for review to the clinician with an overlay for the selected image frames that identifies the abnormalities with graphical or textual indicia. The overlay further may be annotated by the clinician and stored to create documentary record of the fetal ultrasound examination.

23 Claims, 4 Drawing Sheets

(56) References Cited

U.S. PATENT DOCUMENTS

| | | | |
|---|---|---|---|
| 2005/0004465 A1* | 1/2005 | Abuhamad | A61B 8/463 600/443 |
| 2014/0050384 A1 | 2/2014 | Schmidt et al. | |
| 2020/0155114 A1* | 5/2020 | Park | A61B 8/0883 |
| 2020/0214618 A1* | 7/2020 | Vullings | G16H 50/20 |
| 2020/0345261 A1* | 11/2020 | Haeusser | A61B 5/361 |
| 2021/0034587 A1 | 2/2021 | Arye et al. | |
| 2021/0150693 A1* | 5/2021 | Fornwalt | G16H 50/30 |
| 2021/0345987 A1 | 11/2021 | Ciofolo-Veit et al. | |
| 2022/0012875 A1 | 1/2022 | Arnaout | |
| 2022/0142609 A1* | 5/2022 | Yeo | A61B 8/461 |
| 2022/0361799 A1* | 11/2022 | Hong | A61B 8/5284 |
| 2023/0064623 A1* | 3/2023 | Krishnan | A61B 8/0866 |
| 2023/0135046 A1* | 5/2023 | Liu | G06T 7/0014 600/440 |

OTHER PUBLICATIONS

Alom, et al., The History Began from AlexNet: A Comprehensive Survey on Deep Learning Approaches, retrieved from the internet URL: https://arxiv.org/abs/1803.01164, 39 pages (2018).
Arnaout, et al., An Ensemble of Neural Networks Provides Expert-Level Prenatal Detection of Complex Congenital Heart Disease, *Nature Medicine*, 27(5):882-891 (May 2021).
Carreira, et al., Quo Vadis, Action Recognition? A New Model and the Kinetics Dataset, retrieved from the internet URL: https://arxiv.org/abs/1705.07750, 10 pages (2018).
Carvalho, et al., ISUOG Practice Guidelines (updated): sonographic screening examination of the fetal heart, Ultrasound Obstet. Gynecol., 41:348-359 (2013).
Cluster, Construct Clusters from Gaussian Mixture Distribution, retrieved from the internet URL: https://www.mathworks.com/help/stats/gmdistribution.cluster.html, 6 pages, retrieved on Apr. 13, 2023.
Cluster Gaussian Mixture Data Using Hard Clustering, retrieved from the internet URL: https://www.mathworks.com/help/stats/cluster-data-from-mixture-of-gaussian-distributions.html, retrieved on Apr. 13, 2023, 6 pages.
Cluster Gaussian Mixture Data Using Soft Clustering, retrieved from the internet URL: https://www.mathworks.com/help/stats/cluster-gaussian-mixture-data-using-soft-clustering.html, retrieved on Apr. 13, 2023, 5 pages.
Create Gaussian Mixture Model, retrieved from the internet URL: https://www.mathworks.com/help/stats/gmdistribution.html#mw_132ef7d2-0aa5-498f-bd6e-824f3edc8567, retrieved on Apr. 13, 2023, 8 pages.
Data Sets, UCF101—Action Recognition Data Set, UCF Center for Research in Computer Vision, 6 pages (2012).
Day, et al., Artificial Intelligence, Fetal Echocardiograhy, and Congenital Heart Disease, Prenatal Diagnosis, 41(6):733-42 (May 2021).
Donofrio, et al., Diagnosis and Treatment of Fetal Cardiac Disease, A Scientific Statement From the American Heart Association, *Circulation*, 129(21):2183-242 (May 2014).
Feichtenhofer, et al., Convolutional Two-Stream Network Fusion for Video Action Recognition, retrieved from the internet URL: https://arxiv.org/abs/1604.06573, 9 pages (2016).
Feichtenhofer, et al., Slow Fast Networks for Video Recognition, retrieved from the internet URL: hhttps://arxiv.org/abs/1812.03982, 10 pages (2019).
Feichtenhofer, et al., Spatiotemporal Residual Networks for Video Action Recognition, retrieved from the internet URL: https://arxiv.org/abs/1611.02155, 9 pages (2016).
Fitgmdist, Fit Gaussian Mixture Model to Data, MATLAB fitgmdist, retrieved from the internet URL: https://www.mathworks.com/help/stats/fitgmdist.html, retrieved on Apr. 13, 2023, 17 pages.
Gao, et al., Fast Video Multi-Style Transfer, IEEE Winter Conference on Applications of Computer Vision (WACV), pp. 3222-3230 (2020).

Gatys, et al., A Neural Algorithm of Artistic Style, retrieved from the internet URL: https://arxiv.org/abs/1508.06576, 16 pages (2015).
Gkioxari, et al., Finding Action Tubes, retrieved from internet URL: https://arxiv.org/abs/1411.6031, 10 pages (Nov. 2014).
Goodale, et al., Separate Visual Pathways for Perception and Action, Trends in Neurosciences, 15(1):20-25 (Jan. 1992).
Grandjean, et al., The performance of routine ultrasonographic screening of pregnancies in the Eurofetus Study, *American Journal of Obstetrics and Gynecology*, 181(2):446-454 (Aug. 1999).
He, et al., Deep Residual Learning for Image Recognition, In Proceedings of the IEEE Conference on Computer Vision and Pattern Recognition, pp. 770-778 (2016).
HMDB: A Large Human Motion Database, Serre Lab, retrieved from the internet URL: https://serre-lab.clps.brown.edu/resource/hmdb-a-large-human-motion-database/, accessed on Mar. 23, 2023, 6 pages.
Howard, et al., Improving Ultrasound Video Classification: an Evaluation of Novel Deep Learning Methods in Echocardiography, Journal of Medical Artificial Intelligence, 14 pages (Mar. 2020).
Huang, Real-Time Neural Style Transfer for Videos, IEEE Conference on Computer Vision and Pattern Recognition (CVPR), 9 pages (2017).
Image Gradient, Wikipedia The Free Encyclopedia, retrieved from the internet URL: https://en.wikipedia.org/wiki/Image_gradient, accessed on Mar. 23, 2023, 3 pages.
Ioffe, et al., Batch Normalization: Accelerating Deep Network Training by Reducing Internal Covariate Shift, retrieved from internet URL: https://arxiv.org/abs/1502.03167, 11 pages (2015).
Ji, et al., 3D Convolutional Neural Networks for Human Action Recognition, IEEE Transactions on Pattern Analysis and Machine Intelligence, 35(1), 8 pages (Jan. 2013).
Krizhevsky, et al., ImageNet Classification with Deep Convolutional Neural Networks, Communications of the ACM, 60(6):84-90 (Jun. 2017).
Levy, et al., Fetal Echocardiography: 5-4-3-2-1, The Levy-Stos Method, Gynecologie Obstetrique Pratique, No. 309 (Nov. 2018) (w-English Translation).
Liu, et al., Generalize Ultrasound Image Segmentation via Instant and Plug & Play Style Transfer, retrieved from internet URL: https://arxiv.org/abs/2101.03711, 5 pages (2021).
Liu, et al., Remove Appearance Shift for Ultrasound Image Segmentation via Fast and Universal Style Transfer, retrieved from internet URL: https://arxiv.org/abs/2002.05844, 6 pages (2020).
Optical flow, Wikipedia The Free Encyclopedia, retrieved from the internet URL: https://en.wikipedia.org/wiki/Optical_flow, accessed on Mar. 23, 2023, 6 pages.
Ouyang, et al., Interpretable AI for Beat-to-Beat Cardiac Function Assessment, Stanford University, 23 pages (2019).
Pan, et al., An Improved Two-stream Inflated 3D ConvNet for Abnormal Behavior Detection, Intelligent Automation and Soft Computing, 29(3):673-688 (Jan. 2021).
Qiu, et al., Learning Spatio-Temporal Representation with Pseudo-3D Residual Networks, retrieved from the internet URL: https://arxiv.org/abs/1711.10305, 9 pages (2017).
Ruder, et al., Artistic Style Transfer for Videos and Spherical Images, International Journal of Computer Vision, 19 pages (2018).
Simonyan, Two-Stream Convolutional Network for Action Recognition in Videos, Visual Geometry Group, University of Oxford, 9 pages (2014).
Simonyan, Very Deep Convolutional Networks for Large-Scale Image Recognition, Visual Geometry Group, University of Oxford, 14 pages (2015).
Sun, et al., Human Action Recognition using Factorized Spatio-Temporal Convolutional Networks, retrieved from the internet URL: https://arxiv.org/abs/1510.00562, 9 pages (2015).
Szegedy, et al., Going Deeper with Convolutions, 2015 IEEE Conference on Computer Vision and Pattern Recognition (CVPR), 9 pages (Jun. 2015).
Szegedy, Going Deeper with Convolutions, IEEE Conference on Computer Vision and Pattern Recognition (CVPR), 12 pages (2014).
Tran, et al., A Closer Look at Spatiotemporal Convolutions for Action Recognition, retrieved from the internet URL: https://arxiv.org/abs/1711.11248, 10 pages (2018).

(56) References Cited

OTHER PUBLICATIONS

Tran, et al., Learning Spatiotemporal Features with 3D Convolutional Networks, IEEE International Conference on Computer Vision (ICCV), 16 pages (2015).

Tune Gaussian Mixture Models, retrieved from the internet URL: https://www.mathworks.com/help/stats/tune-gaussian-mixture-models.html, retrieved on Apr. 13, 2023, 7 pages.

Varol, et al., Long-term Temporal Convolutions for Action Recognition, retrieved from the internet URL: https://arxiv.org/abs/1604.04494, 8 pages (2017).

Vivaaindrean, Detection of Robbery-Related Concepts Using Deep Learning, Final Year Project, UTAR, 56 pages (Jan. 2020).

Wang, et al., Actions ~ Transformations, retrieved from the internet URL: https://arxiv.org/abs/1512.00795, 10 pages (2016).

Wang, et al., Towards Good Practices for Very Deep Two-Stream ConvNets, retrieved from the internet URL: https://arxiv.org/abs/1507.02159, 5 pages (2015).

Wolfe, Deep Learning on Video (Part One): The Early Days, retrieved from the internet URL: https://towardsdatascience.com/deep-learning-on-video-part-one-the-early-days-8a3632ed47d4, 13 pages (2021).

Xie, et al., Rethinking Spatiotemporal Feature Learning: Speed-Accuracy Trade-offs in Video Classification, retrieved from the internet URL: https://arxiv.org/abs/1712.04851, 17 pages (2018).

\* cited by examiner

Normal 4 chamber view showing foramen ovale

View showing large atrioventricular defect

SYSTEMS AND METHODS FOR IMPROVING DETECTION OF FETAL CONGENITAL HEART DEFECTS

CROSS-REFERENCE TO RELATED APPLICATIONS

This application claims priority to EP Patent Application Serial No. 23305235.6, filed Feb. 22, 2023, the entire contents of which are incorporated herein by reference.

FIELD OF USE

The present invention is directed to systems and methods for improving detection of fetal congenital heart defects during and after ultrasound examination by using machine learning algorithms to ensure creation of a complete dataset, conduct preliminary review of the completed dataset, and determine datasets to be designated for expert review.

BACKGROUND

Congenital heart disease (CHD) is the most common birth defect with a prevalence of about 0.8-1% among all births. As of 2014, in the United States, CHD accounts for 4% of neonatal deaths, and for 30% to 50% of deaths related to congenital anomalies. A study by Nayak, et al. entitled "Evaluation of fetal echocardiography as a routine antenatal screening tool for detection of congenital heart disease," Cardiovasc. Diagn. Ther. 6, 44-49 (2016) demonstrated that 92% of CHD occurred in pregnancy defined as "low risk." Stümpflen, et al., in a study entitled "Effect of detailed fetal echocardiography as part of routine prenatal ultrasonographic screening on detection of congenital heart disease," The Lancet 348, 854-857 (1996) observed that most CHD are identified during the second trimester of pregnancy screening exam, supporting the need for a universal fetal heart screening exam during the second trimester of the pregnancy.

CHD is often asymptomatic in fetal life but causes substantial morbidity and mortality after birth. In addition to adverse cardiac outcomes, CHD is associated with an increased risk for adverse neurodevelopmental outcomes, associated with factors such as associated chromosomal abnormalities, syndromes, postnatal cardiac dysfunction, and in utero hemodynamic abnormalities. Critical CHD (see Table 1), defined as requiring surgery or catheter-based intervention in the first year of life, accounts for approximately 25 percent of all CHD. See, Oster, M.E. et al., "Temporal trends in survival among infants with critical congenital heart defects," Pediatrics 131, e1502-1508 (2013). In infants with critical cardiac lesions, the risk of morbidity and mortality increases when there is a delay in diagnosis and timely referral to a tertiary center with expertise in treating these patients. See Kuehl, K.S., et al. "Failure to Diagnose Congenital Heart Disease in Infancy," Pediatrics, 103:743-7 (1999): Eckersley, L., et al., "Timing of diagnosis affects mortality in critical congenital heart disease," Arch. Dis. Child. 101, 516-520 (2016).

Compared to postnatal diagnosis, fetal diagnosis can dramatically improve neonatal outcomes by anticipating delivery care, surgical and/or early interventional planning and in some cases, considering in utero therapies. Further, accurate antenatal diagnosis allows the parents to make an informed decision regarding the continuation of pregnancy. Distinguishing normal fetal hearts from those exhibiting complex forms of CHD typically involves an initial screening exam performed by physicians, nurse practitioners, physician assistants, ultrasound technicians, and other providers trained in diagnostic obstetric ultrasonography. Licensed medical providers who meet the training specialty guidelines are responsible for the interpretation of the ultrasound examination. Further examination via fetal echocardiography is warranted if the ultrasound is abnormal for confirmation and diagnosis refinement. Further examination may also be warranted under circumstances such as a family history of congenital heart defect, presence of maternal diabetes, or use of in vitro fertilization. Only well-trained and/or experienced pediatric cardiologists, maternal-fetal medicine specialists, obstetricians, or radiologists who have acquired the appropriate knowledge base and skills supervise and perform such fetal echocardiograms. Low sensitivity in this task can limit palliation options, worsen postnatal outcomes and hamper research on in utero therapies, while low specificity can cause unnecessary additional testing and referrals.

The World Health Organization (WHO) recommends that all pregnant women have one ultrasound scan before 24 weeks of pregnancy to estimate gestational age (GA), assess placental placement, determine single or multiple pregnancies, increase fetal abnormality detection, and improve pregnancy outcomes. WHO Recommendations on Antenatal Care for a Positive Pregnancy Experience (World Health Organization, 2016).

In 2013 and 2018, both the American Institute of Ultrasound in Medicine (AIUM) and the International Society of Ultrasound in Obstetrics and Gynecology (ISUOG) changed their practice guidelines for fetal heart screening of mid-gestation fetuses. See, Carvalho et al., "ISUOG Practice Guidelines (updated): sonographic screening examination of the fetal heart: ISUOG Guidelines," Ultrasound Obstet. Gynecol. 41, 348-359 (2013); "AIUM-ACR-ACOG-SMFM-SRU Practice Parameter for the Performance of Standard Diagnostic Obstetric Ultrasound Examinations," J. Ultrasound Med. 37, E13—E24 (2018). These updated guidelines specified a minimum of three views: the four-chamber view (4C) and views of the left (LVOT) and right (RVOT) ventricular outflow tracts (2, 3). Unfortunately, several heart malformations are not well detected prenatally with this approach. While the three-vessel (3V) and three-vessels-and-trachea (3VT) views are not mandatory in the AIUM and ISUOG practice guidelines, both guidelines state that these views are desirable and should be attempted as part of routine screening. See Table 2. Many groups already perform additional views during routine screening and report higher fetal heart malformation detection rates, of 62-87.5%, compared with 40-74% using the recommended three views, as described in "Committee on Practice Bulletins—Obstetrics and the American Institute of Ultrasound in Medicine, Practice Bulletin No. 175: Ultrasound in Pregnancy," Obstet. Gynecol. 128, e241-e256 (2016).

Some critical CHD are more amenable to visualization through ultrasound screening during the pregnancy than others. Using 1997-2007 data from the Utah Birth Defect Network, Pinto et al., in "Barriers to prenatal detection of congenital heart disease: a population-based study," Ultrasound Obstet. Gynecol. Off. J. Int. Soc. Ultrasound Obstet. Gynecol. 40, 418-425 (2012), observed that the defects most likely to be detected prenatally included those with abnormal four-chamber views, while defects exhibiting abnormal outflow tracts were much less likely to be detected prenatally. In a study of members of a large health maintenance organization (HMO) in California from 2005 to 2010, Levy et al., in "Improved prenatal detection of congenital heart disease in an integrated health care system," Pediatr. Cardiol. 34, 670-679 (2013), showed that women who received care from HMO clinics that had instituted a policy to examine outflow tracts during prenatal ultrasound had much higher prenatal diagnosis rates (59%) compared to HMO clinics that had not instituted such a policy (28%).

In current triaging workflows, a patient typically presents at a first point of care (OB-Gyn, Midwife or radiologist), where an assessment of the fetus is performed, e.g., via a fetal ultrasound screening performed by the healthcare professional or by a sonographer. The image data is interpreted in real time by a first line practitioner during the ultrasound exam or off line, after the exam has been performed. The report is generated by the first line practitioner and might be pre-filled in by the sonographer. If a congenital heart defect is suspected, the patient is referred to a specialist who will review the report, and perform a specific exam (echocardiography, genetic test) intended to confirm the presence or absence of the potential congenital defect. Depending upon the outcome of that further exam or test, a decision is made regarding treatment and/or transfer of the patient to a follow-up point of care.

Drawbacks to previously-known CHD screening workflow are numerous, and generally include: inaccuracy and low specificity caused by improper examination technique, time pressure, obesity of the mother, and simple misdiagnosis. In particular, CHD detection during a second trimester ultrasound exam is often as low as 30%. Specificity also is suboptimal, as low as 40-50% due to a lack of skill in adapting ultrasound images (i.e., ultrasound operator lacks the skill needed to obtain data from which a correct diagnosis can be made, resulting in about 49% of the misdiagnoses; lack of experience in formulating an accurate diagnosis (i.e., the images obtained are sufficient and the prenatal pathology is visible, but not recognized by the operator, resulting in about 31% of the misdiagnoses; the pathologies cannot be detected because they are not visible on the ultrasound images, accounting for about 20% of missed diagnoses. Time pressures associated with achieving adequate patient throughput in the clinical setting can exacerbate the foregoing issues, especially when transfer of a patient to a specialist is required.

While some efforts have been made to improve CHD detection during routine prenatal ultrasound examination, much is left to be done. For example, there is considerable guidance available to ultrasound technicians describing how to obtain a complete, high diagnostic quality dataset of images during an examination, and how to confirm the presence of cardiac structure in real time during an examination. For example, U.S. Pat. No. 7,672,491 to Krishnan et al. describes a system for evaluating the diagnostic quality of images acquired during an ultrasound examination that uses machine learning to compare the acquired images to expected images.

As discussed above, the ISUOG Practice Guidelines, published in *Ultrasound Obstet. Gynecol.* 2013; 41:348-359 suggests five axial locations that should be imaged during a routine fetal heart ultrasound examination, as well as the principal organs and vessels and orientations of each that should be confirmed at each location. European Patent Application Publication EP 3964136 to Voznyuk et al. describes a machine learning system that analyzes ultrasound images generated during an examination, uses a first convolutional neural network (CNN) to compare acquired images to views required by those guidelines, and a second CNN to analyze the images to identify potential abnormalities.

U.S. Patent Application Publication No. US 2021/0345987 to Ciofolo-Veit et al. describes an ultrasound imaging system that uses machine learning algorithms to analyze acquired images to detect anomalous features, and if an anomalous feature is detected, uses machine learning algorithms to determine and display other previously-acquired ultrasound images that provide complementary views of the potential anomalous feature to permit improved diagnosis.

In addition, a fetal ultrasound screening examination typically generates thousands of image frames spanning multiple structures per single video "sweep," so the diagnostic frames of interest for CHD may be only a handful and thus are easily missed. Moreover, the prevalence of CHD in the population (~0.8-1%) is low enough that non-experts see it only rarely and may discount or overlook abnormal images. Together, these factors make CHD detection one of the most difficult diagnostic challenges in ultrasound, with a dramatic impact on post-natal outcomes and quality of life.

In view of the foregoing, it would be desirable to provide methods and apparatus for triaging prenatal ultrasound scanning to improve accuracy of congenital defect detection, and subsequent management.

It further would be desirable to provide a machine-learning enabled system for pre-natal fetal ultrasound configured to review recorded ultrasound video and to identify images from the video that correspond to the views recommended by the guidelines.

It still further would be desirable to provide methods and systems for conducting prenatal ultrasound examinations that assist the sonographer in collecting a high-quality dataset in accordance with applicable guidelines, assist the interpreting physician and/or technician in identifying potential abnormalities in the acquired data, and moreover, in real time guides the sonographer to acquire additional views to augment the image dataset, e.g., to facilitate specialist review.

It still further would be desirable to provide methods and systems for objectively evaluating the performance of the sonographer over multiple exams.

SUMMARY

The present invention is directed to systems and methods for conducting fetal ultrasound examinations that aids in the detection of critical heart defects during a second semester ultrasound exam. The inventive systems and methods help trained and qualified physicians to interpret ultrasound recording motion video clips by identifying standard views appearing within motion video clips. In addition, the systems and methods of the present invention may assist in detecting and identifying morphological abnormalities that might be indicative of critical CHDs. For example, Table 3 provides an exemplary correspondence between representative CHDs, the views in which those CHDs usually appear, and the morphological abnormalities that typically can be identified in those views.

In one embodiment, the systems and methods are embodied in a computer assisted diagnostic aid for use in two-dimensional prenatal ultrasound exams of fetuses, such as usually performed during the second trimester of pregnancy. Machine learning algorithms are employed to assist users with the identification and interpretation of standard views in fetal cardiac ultrasound motion video clips. In particular, the inventive systems and methods are embodied in software that may be executed to support identification of critical CHDs. In addition, information generated during the machine learning augmented analyses may be stored for later referral to an expert (e.g., specialist) to assist further diagnosis and treatment planning.

In a preferred embodiment, the inventive system employs two components: a user interface component that provides a clinician tools to analyze and review fetal ultrasound images and ultrasound motion video clips, and a machine learning interpretative component that receives ultrasound motion video clips and images from a conventional fetal ultrasound screening system, identifies images within the motion video clips that correspond to fetal ultrasound screening guidelines. The interpretative component also analyzes the identified images to detect and identify the presence of morphological abnormalities, and provides that information to the user interface component to highlight such abnormalities for the clinician's review. The interpretative component may be executed partially or fully on a local computer workstation in real-time. Alternatively, the interpretative component may reside on a cloud-based server and interact with the user interface component via a secure connection on a local or wide area network, such as the Internet.

In accordance with another aspect of the invention, the methods and systems provide a consistent process to ensure that all views suggested by the practice guidelines for fetal exams are acquired. In particular, if the machine-learning based review of the motion video clips from the fetal ultrasound scan does not identify an image frame determined as appropriate for review, the system will flag that view as being unavailable or of inadequate quality to permit analysis for abnormality detection, the user interface will direct the clinician to re-perform the ultrasound scan to acquire the missing data. The new motion video clip then is transmitted to the interpretive component for analysis and a supplemental analysis will be returned to the user interface for presentation to the clinician.

In accordance with another aspect of the invention, the analysis results returned to the user interface component may be displayed and further annotated by the clinician to include additional graphical indicia or textual remarks. The resulting analysis results and annotations may be stored for later referral to an expert to develop a plan for further diagnosis or treatment.

In accordance with another aspect of the invention, analysis and/or results, including detected morphological abnormalities, may be used to generate a report. The report may be automatically populated with entries for each standard view using frames of video clips, which may include bounding box overlays. Information about the view may be included in the report to add context to the images.

In accordance with another aspect of the invention, the system may recommend a referral to a clinician and/or expert. In accordance with another aspect of the invention, the system may perform an objective evaluation of the technician that performed the imaging (e.g., the sonographer). In accordance with another aspect of the invention, the system may automatically organize the results with the most relevant information appearing first or otherwise most prominently. Additionally, or alternatively, the results may be organized by patient in order of severity.

BRIEF DESCRIPTION OF THE DRAWINGS

FIGS. 4A and 4B are exemplary images presented to a clinician via the user interface module after analysis results are returned from the interpretive module, in which FIG. 4A shows an image selected as corresponding to the four chambers view and FIG. 4B is a similar view for a different fetus including a bounding box identifying a large atrioventricular defect.

DETAILED DESCRIPTION OF THE INVENTION

Systems and methods are disclosed for conducting fetal ultrasound examinations that aid in the detection of critical heart defects during a fetal ultrasound exam, typically conducted during the second trimester. In particular, the inventive systems and methods assist trained and qualified physicians to interpret ultrasound recording motion video clips by identifying and selecting for presentation to the physician image frames corresponding to standard guidelines views that appear within motion video clips. More specifically, the systems and methods of the present invention assist in detecting and identifying morphological abnormalities that may be indicative of critical CHDs. Table 3 provides an exemplary correspondence between representative CHDs, the views in which those CHDs usually appear, and the morphological abnormalities that typically can be identified in those views.

Figure 1:
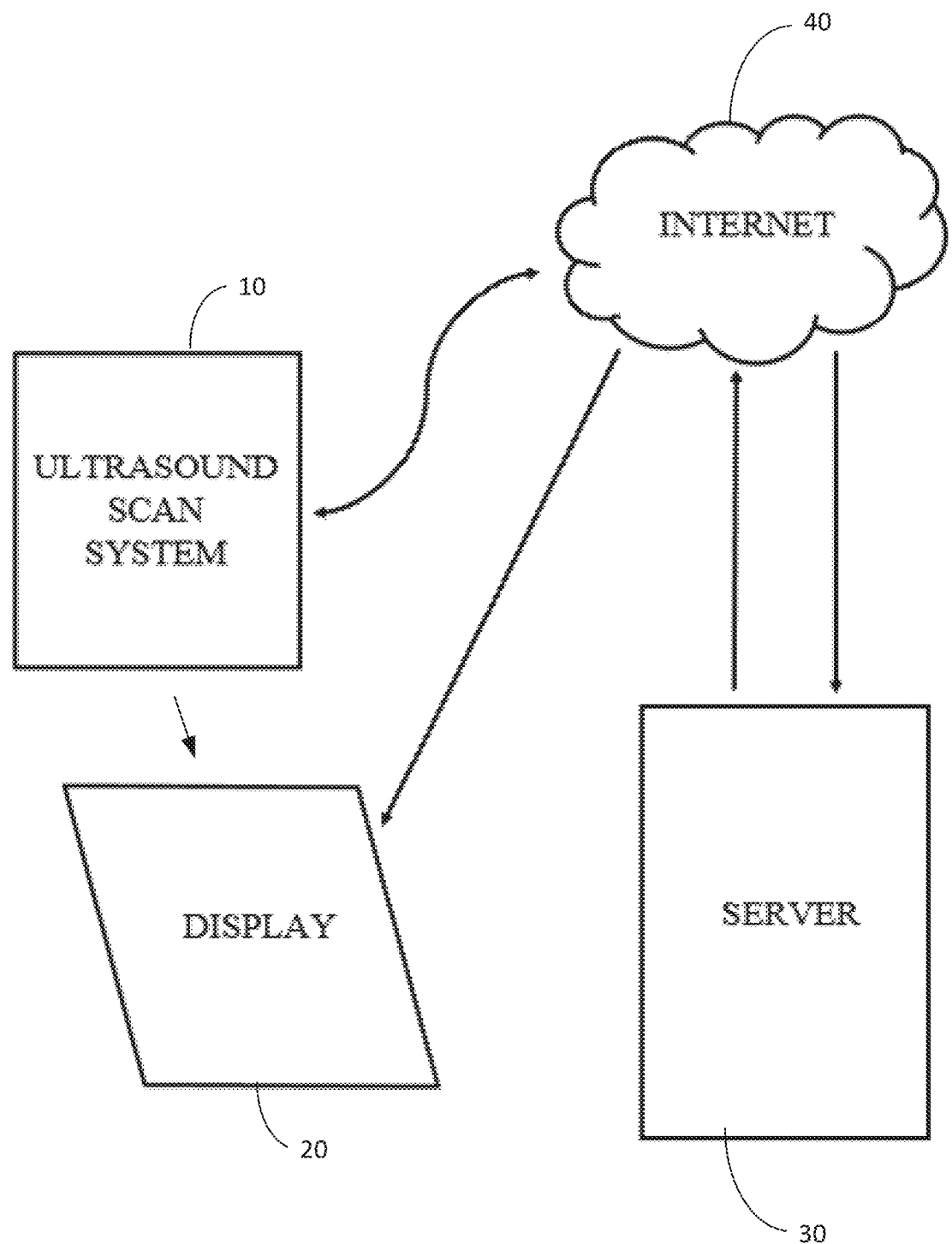
FIG. 1 is a schematic view of an exemplary server-based model for implementing the methods and systems of the present invention.

In an exemplary system depicted in FIG. 1, the system may include a conventional ultrasound system 10, display computer 20, and server system 30 that communicate with each other via wide area network 40, illustratively, the Internet. In a preferred embodiment, the systems and methods are embodied in a computer assisted diagnostic aid for use in two-dimensional fetal ultrasound exams, such as usually performed during the second trimester of pregnancy. Machine learning algorithms are employed to assist users with the identification and interpretation of standard views in fetal cardiac ultrasound motion video clips.

In one preferred embodiment, the inventive methods and systems employ two software components: a user interface component and an interpretative component. The user interface computer preferably is resident on display computer 20, and provides a clinician tools to analyze and review fetal ultrasound images and ultrasound motion video clips. The interpretative component preferably resides on server computer 30, receives ultrasound motion video clips and images from ultrasound system 10 or display computer 20, and uses machine learning algorithms to identify images within the motion video clips that correspond to fetal ultrasound screening guidelines. The interpretative component also analyses the identified images as well as any non-identified images (e.g., corresponding to non-standard or non-recommended views) to detect and identify the presence of morphological abnormalities, and provides that information to the user interface component to highlight such abnormalities for the clinician's review. In an alternative embodiment, the interpretive component may be executed partially or fully on a local computer workstation in real-time.

As is typical, ultrasound system 10 includes a handheld probe that a clinician moves across a patient's abdomen to generate motion video clips of the fetus during a pre-natal fetal examination, which clips may be transmitted to display computer 20 during the scanning process for storage and display on a display screen associated with display computer 20. The motion video clips generated during the examination may be directly uploaded from ultrasound system 10 to server system 30 via wide area network 40, or may be transmitted by a user interface module executing on display computer 20.

Display computer 20 preferably is configured to display real-time video generated by ultrasound system 10, and in addition, is configured to display to the clinician analysis results generated by the interpretive component executing on server system 30. Display computer may include a display screen, storage, CPU, input devices (e.g., keyboard, mouse) and network interface circuitry for bi-directionally communicating with server system 30 via wide area network 40. In a preferred embodiment, display computer 20 executes the user interface component of the invention, which accepts and stores physiologic information about the patient. Display computer 20 also receives and stores real-time ultrasound video from ultrasound system 10 and relays that image data, together with the patient's physiologic information, to the interpretative component that executes on server system 30.

Server system 30 includes the interpretive component of the inventive system, including machine learning algorithms for analyzing the motion video clips received from display compute 20 to compare the ultrasound video clips to a set of the preferred image templates that correspond to the fetal ultrasound examination guidelines. In a preferred embodiment, the interpretive component includes image templates that correspond to each of the views recommended in the fetal heat ultrasound screening guidelines set forth in Table 2, including: (1) the transverse abdominal view; (2) the four chamber view (4C); (3) left ventricular outflow tract view (LVOT); (4) right ventricular outflow tract view (RVOT); (5) the three vessel view (3V) and (6) the three vessel and trachea view (3VT). As described in further detail below, the interpretative component preferably employs machine learning to compare each frame of the input motion video clips to the six foregoing view templates, and selects one or more high quality image frames as corresponding to the selected template. If an abnormality is detected, an image frame showing the abnormality may be selected. The interpretative component employs a machine learning model to analyze each of the image frames, selected as representative of the guideline views, and optionally other non-selected image frames, for the presence of the abnormalities known to be present in those image templates as set forth in Table 3.

For example, one the interpretive component has identified and selected an image frame from an uploaded motion video clip as representative of the 3VT view, the machine learning feature will analyze the selected image frame for features identified in Table 3 as being visible in the 3VT view: aorta greater than pulmonary artery, associated with coarctation of the aorta and conotruncal lesions; right aortic arch, associated with conotruncal lesions; abnormal vessel alignment, associated with transposition of the great arteries; and additional visible vessel, associated with anomalous pulmonary venous connection.

If the interpretative component of the system identifies one or more of the features described in Table 3 as being present in the selected image frame, the system further may create an overlap on the selected image that includes a bounding box that surrounds the detected abnormality and optionally, a textual label associated with the suspected defect. The selected image frames and analytical results then are transmitted back to display computer 20 for presentation to, and consideration by, the clinician. As clinicians often have multiple patients, the clinician may be sent or may otherwise be tasked with reviewing results from several patients. To facilitate efficient review by the clinician and/or expert, the system may automatically organize the results with the most relevant information, such as detected morphological abnormalities, appearing first or otherwise most prominently. Additionally, or alternatively, the results may be organized by patient in order of severity.

Display computer 20 may provide the ability to annotate the selected image frames with additional graphical or textual notes, which are then saved with the results for later recall during preparation of a documentary report concerning the fetal ultrasound examination.

If during analysis by the interpretative component no motion video clip image frame is identified as corresponding to a standard view template, or the identified image frame is adjudged to be of too poor quality to permit analysis for potential defects, that image template is identified as missing when the analysis results are transmitted back to display computer 20. In this case, the clinician may be prompted by display computer 20 to rescan the fetus to acquire the missing view, and that motion video clip may be resubmitted to the interpretative component for supplemental analysis. The results of the supplemental analysis may then be sent back to display computer 20 for presentation to, and consideration by, the clinician.

Figure 2:
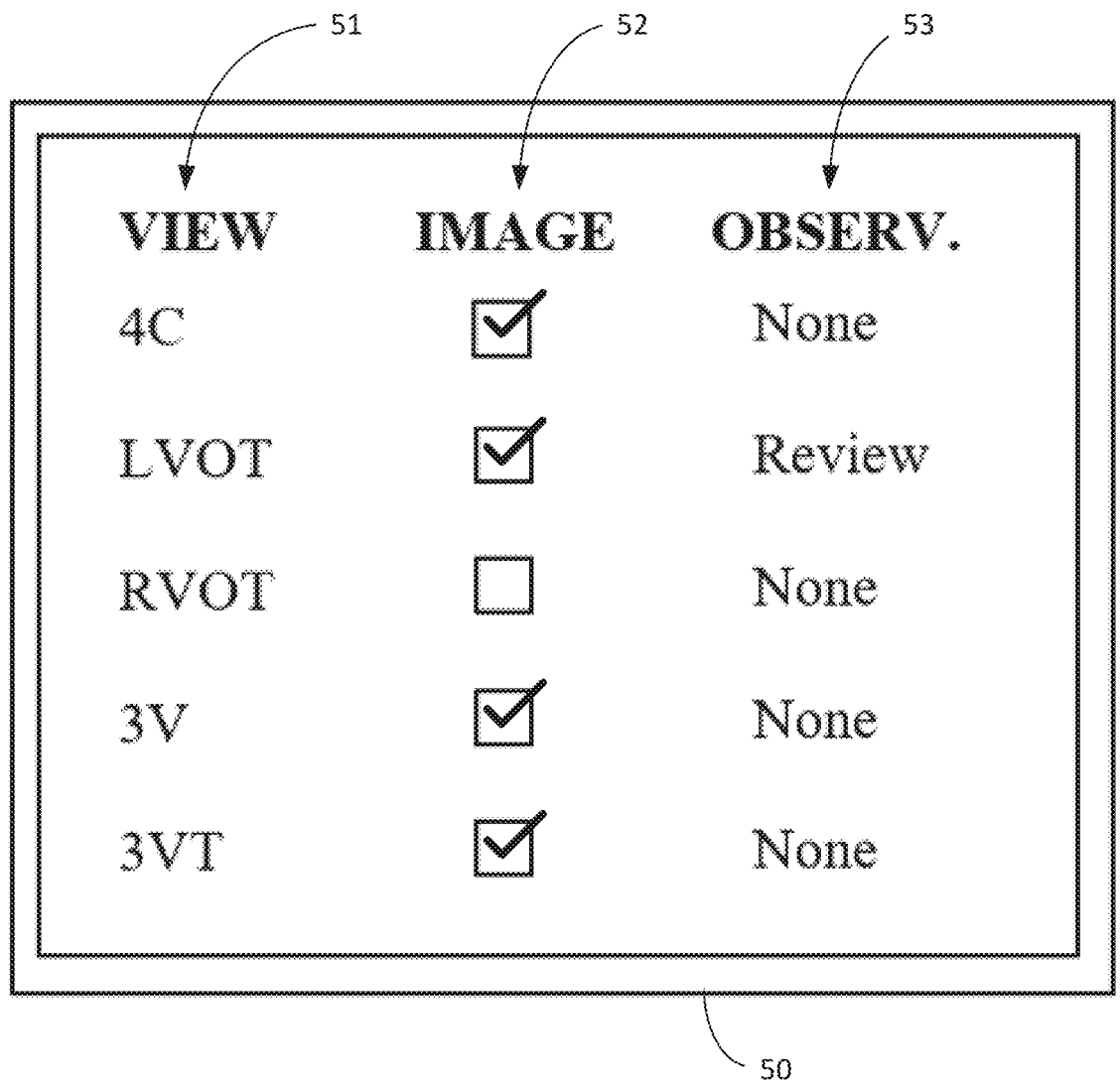
FIG. 2 is an exemplary screen display presented to the clinician showing the results returned to the user interface by the interpretive component.

Referring now to FIG. 2, an exemplary display suitable for summarizing the results returned to display computer 20 by the interpretative component residing on server system 30 is described. Display 50 includes three columns 51-53, which may include links that can be activated using the input device, e.g., a mouse, associated with display computer 20. Column 51, labeled "View," describes the standard guidelines views (e.g., 4C, LVOT, etc.). Column 52, labeled "Image," includes checkboxes indicating whether the interpretative component of the system has identified and selected an image frame as corresponding to the standard guidelines view. Column 53, labeled "Obser," denotes whether any observations, such as potential abnormalities, have been detected in a selected image frame.

Activating a link in the View column, column 51, such as by clicking on the view title with a mouse, will display an idealized generic image of the standard guideline view, such as those shown in Table 2. In column 52, the presence of a checkbox indicates that an image frame was selected by the interpretative component on server computer 30. Clicking on that checkbox will cause the display computer to display the raw image selected by the interpretative component. The absence of a checkbox in column 52 indicates that the interpretative component was unable to locate an image in the motion video clips suitable for analysis by the machine learning feature. Clicking on the empty checkbox, for example, for RVOT in FIG. 2, may be configured to display a prompt to the clinician to rescan a portion of the patient's abdomen to acquire a new motion video clip containing the desired view, which then may be sent to server computer 30 for supplemental analysis.

Column 53 may include textual descriptions for any observations noted by the interpretative component in the selected image frames. For example, in FIG. 2, column 53 presents the labels "None" for all views except the RVOT view. Because display 50 may be visible to the patient, column 53 preferably uses neutral labeling, "Review," to indicate to the clinician that a potential abnormality was detected in that view, rather than a more descriptive label that could cause undue concern to the patient. In one embodiment, the textual indicators for each standard view may be clickable links. For example, clicking on a label that states "None" for the 4C, LVOT, 3V and 3VT views in FIG. 2 may display the image frame selected by the interpretative component along with labels that indicate where the interpretative component adjudged the anatomical landmarks to be located. On the other hand, clicking on the label "Review" for the RVOT view in FIG. 2 may display the selected image frame, labeled anatomical landmarks, and a bounding box surrounding the suspected abnormality, along with a textual description of the potential defect.

In a fetal ultrasound examination conducted in accordance with the principles of the present invention, following review of the real-time ultrasound motion video clips generated by the ultrasound scanner 10 as displayed on display computer 20, the clinician then may review the analysis results generated and returned by the interpretative component residing on server computer 30. In this manner, the clinician may review the contents of display 50 of FIG. 2, review the selected raw image data corresponding to each standard guideline view (by clicking on the checkboxes in column 52), and review the detailed machine learning analysis of that selected image frame by clicking on the labels in column 53. The clinician therefore may be able to corroborate his or her own observations during review of the real-time video clips or adjust his or her findings based on the machine learning analysis results. As noted above, display computer 20 may include the ability to open additional boxes associated with any of the image frames presented in column 53 to record and store additional findings for later recall in preparing a written or electronic report documenting the fetal ultrasound examination.

Figure 3:
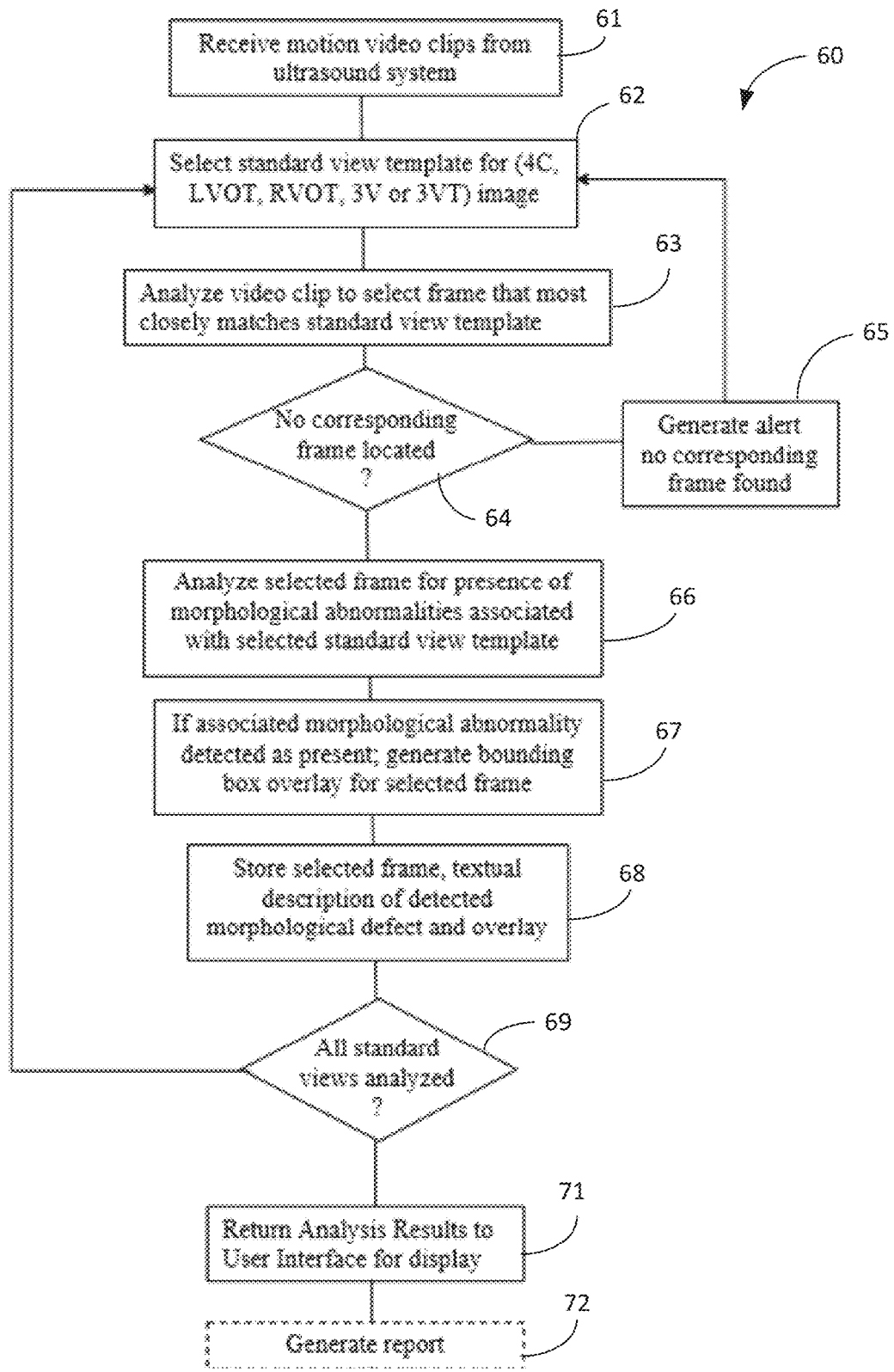
FIG. 3 is an exemplary flowchart showing the analysis process undertaken by the interpretive component to analyze motion video clips generated during a fetal ultrasound examination.

Turning now to FIG. 3, exemplary flowchart 60 for the interpretative component of the analysis software is described. At step 61, motion video clips are received from ultrasound system 10 or display computer 20. At step 62, a template corresponding to a standard guideline view is selected, e.g., 4C, LVOT, RVOT, 3V or 3VT. The template may consist of an idealized version of the images shown in Table 2. At step 63, the received video image clips are analyzed using a machine learning algorithm, e.g., convolutional neural network and/or deep neural network, to compare each frame of the received motion video clip to the standard template to determine which frame or frames best match the standard view guideline template. The interpretative component also may analyze the selected image frame or frames to confirm that the image meets specified quality requirements for clarity. If no frame in a video clip is determined to correspond to the standard view, at decision box 64, the process moves to step 65, where a flag is set indicating that no suitable image frame is available, and the process continues with selection of the next standard view template at step 62.

If the interpretative component adjudges that a corresponding frame is available in the received motion video clip, the process moves to step 66, where the selected image frames, and optionally non-selected image frames, are analyzed by another machine learning algorithm to detect the presence of an abnormality associated with that standard view. For example, if the selected image frame corresponds to the 4C standard view template, the algorithm will analyze the selected frame for the presence of any of the defects listed in Table 3 for that standard view. If a defect is detected in the selected image frame, the algorithm may look at adjacent frames of the video clip to confirm the presence of the same defect. At step 67, an overlay may be created for the selected image frame that includes graphical pointers to the detected anatomical landmarks, as well as a bounding box that surrounds the abnormality detected in the image frame. The overlay also may include textual information that describes the specific abnormality and/or the associated class of CHD, as set forth in Table 3.

At step 68, the information generated by the interpretative component, i.e., the overlay and graphical/descriptive information is associated with the selected image frame and stored in server computer 30 for later transmission to display computer 20. At decision box 69, a determination is made whether all motion video clips have been analyzed for all standard views. If all standard views have not been analyzed or identified as not being present, the process returns to step 62, where the next standard view template is selected for analysis. If at decision box 69 is it determined that all views have been analyzed, or determined not to be present, the process moves to step 70, where the results are returned to display computer 20 for presentation and review by the clinician.

At optional step 72, the analysis and/or results may be used to generate a report. For example, the report may identify detected morphological abnormalities and/or may include an entry for each standard view. For example, detected anomalies may include one or more of abnormal ventricular asymmetry, coarctation of the aorta, pulmonary or aortic valve stenosis, ventricular hypoplasia or univentricular heart and/or any other cardiovascular abnormality. The report may be prepopulated such that, for each standard view entry, a representation image may be selected. If a morphological abnormality is detected, an image representative of the morphological abnormality for a given standard view may be included in the report at the entry for the corresponding view. If a bounding box is generated for a given frame, such image with the bounding box overlay may be used in the report. Information about the view, the anatomy, any textual description of the detected morphological defect and/or abnormality, and/or any other relevant information may additionally be included in the report to add context to the images and otherwise generate a more informative report. The resulting analysis, results, annotations, and/or report may be stored for later reference.

The images, video clips, analysis, results, annotations, and/or report may be shared with or otherwise made available to an expert or clinician (e.g., upon referral to an expert or clinician). Each type of morphological abnormality may be associated with an expert or clinician and their contact information. If a morphological abnormality is detected at step 66, an expert or clinician corresponding to the morphological abnormality may optionally be recommended.

In addition to performing the steps 61-72 illustrated in FIG. 3, the system may perform an objective evaluation of the exam, the images generated, and/or the technician that performed the imaging (e.g., the sonographer). The system may consider data such as the mean duration of the exam and/or image collection, the quality of the images acquired, the percentage of standard views for which a suitable image is acquired, and/or any other information indicative of the quality of the exam, the images and/or the sonographer. For example, a model trained to generate one or more quality values indicative of the quality of the exam and/or images may be used to process such data. The data may be determined over the course of several exams. For example, the percentage of standard views for which a suitable image is acquired for multiple exams by the same technician may be used to determine a quality value indicative of the rate at which a technician performs a complete exam.

Figure 4A:
Figure 4B:
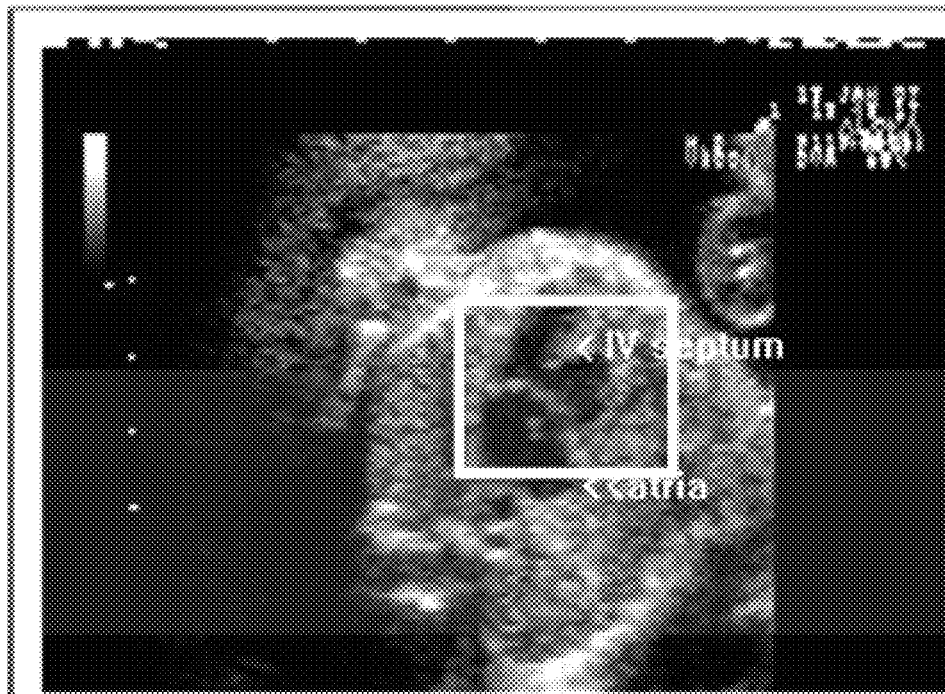

Referring now to FIGS. 4A and 4B, examples of screen displays that may be presented at display computer 20 corresponding to clicking on the text labels identified in FIG. 2 are described. As noted above, if a standard view is identified by the interpretative component as being present in the motion video clips transmitted to server computer 30, a checkmark will appear in column 52 in FIG. 2. As previously described, clicking on the checkbox will cause the raw image selected by the interpretative component to be displayed on display computer 20. Clicking on the "None" label in column 53 will cause the selected image frame, annotated with the overlay generated by the interpretative component, to be displayed on display computer 20. FIG. 4A is an example of an image frame corresponding to a 4C standard view, without abnormalities and with the foramen ovale identified. FIG. 4B is an example of a selected image frame corresponding to a standard 4C view, in which a large atrioventricular defect is detected. In FIG. 4B, the defect is surrounded with a white bounding box; other cardiac structures are identified by textual and graphical labels.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed is:

1. A system for use with an ultrasound system for aiding a clinician in detecting and diagnosing cardiac defects during a fetal ultrasound examination, the system comprising:
   one or more computers configured to store non-transitory programmed instructions, the one or more computers programmed to:
   store view templates corresponding to standard guideline views, including at least view templates for four chamber (4C), left ventricular outflow tract (LVOT), right ventricular outflow tract (RVOT), three vessel (3V) and three vessel and trachea (3VT) views;
   determine, for each view template of the view templates, data indicative of one or more potential abnormalities;
   associate each of the data indicative of one or more potential abnormalities with each respective view template;
   receive a motion video clip generated by the ultrasound system during a fetal ultrasound examination;
   compare, using a first neural network, each frame of the motion video clip to the view templates to identify and select, for each view template, if present, one or more corresponding image frame;
   compare, using a second neural network, each of the one or more corresponding image frame to the data indicative of the one or more potential abnormalities for the view template corresponding to each of the one or more corresponding image frame to detect a presence of the one or more potential abnormalities;
   generate a report indicative of the presence of the one or more potential abnormalities for each of the one or more corresponding image frame; and
   cause a display screen to present, responsive to a request by the clinician, the report including an overlay indicating the presence of the one or more potential abnormalities.

2. The system of claim 1, wherein the one or more computers comprise a display computer and a server computer.

3. The system of claim 2, wherein the non-transitory programmed instructions include a user interface component and an interpretative component.

4. The system of claim 3, wherein the user interface component is configured to receive, store and display in real-time motion video clips generated by the ultrasound system.

5. The system of claim 4, wherein the user interface component is configured to store and display analysis results returned by the interpretative component.

6. The system of claim 3, wherein the interpretative component includes machine learning algorithms for identifying and selecting each of the one or more corresponding image frame.

7. The system of claim 5, wherein the interpretative component further includes machine learning algorithms for detecting the presence of the one or more potential abnormalities in each of the one or more corresponding image frame.

8. The system of claim 1, wherein the overlay indicating the presence of the one or more potential abnormalities includes one or more of a bounding box surrounding a potential abnormality, graphical indicator or textual indicator.

9. The system of claim 1, further comprising non-transitory programmed instructions that enable the clinician to annotate the overlay.

10. The system of claim 1, wherein the report includes the clinician's observations during the fetal ultrasound examination.

11. A method for use with an ultrasound system for aiding a clinician in detecting and diagnosing cardiac defects during a fetal ultrasound examination, the method comprising:
   providing a computer configured to store and execute non-transitory programmed instructions;
   storing on the computer view templates corresponding to standard guideline views, including at least view templates for four chamber (4C), left ventricular outflow tract (LVOT), right ventricular outflow tract (RVOT), three vessel (3V) and three vessel and trachea (3VT) views;
   determining for each view template of the view templates data indicative of one or more potential abnormalities;
   associating each of the data indicative of one or more potential abnormalities with each respective view template;
   generating with an ultrasound system a motion video clip during a fetal ultrasound examination and storing the motion video clip;
   receiving, by the computer, the motion video clip;
   comparing, using a first neural network, each frame of the motion video clip to the view templates to identify and select, for each view template, if present, one or more corresponding image frame;
   comparing, using a second neural network, each of the one or more corresponding image frame to the data indicative of the one or more potential abnormalities for the view template corresponding to the one or more corresponding image frame to detect a presence of the one or more potential abnormalities;
   generating a report indicative of the presence of the one or more potential abnormalities for each of the one or more corresponding image frame; and causing a display screen associated with the computer to present, responsive to a request by the clinician, the report including an overlay indicating the presence of the one or more potential abnormalities.

12. The method of claim 11, wherein providing a computer comprises providing one or more computers including a display computer and a server computer.

13. The method of claim 12, wherein providing the one or more computers comprises providing the display computer with non-transitory programmed instructions for a user interface component and providing a server computer with non-transitory instructions for an interpretative component.

14. The method of claim 13, further comprising displaying to the clinician in real-time with the display computer the motion video clip generated by the ultrasound system.

15. The method of claim 13, further comprising transmitting to the display computer from the server computer analysis results generated by the interpretative component.

16. The method of claim 11, wherein comparing, with the computer, each frame of the motion video clip to the view templates comprising analyzing the motion video clip with machine learning algorithms to identify and select each of the one or more corresponding image frame.

17. The method of claim 11, wherein analyzing, with the computer, each of the one or more corresponding image frame to detect a presence of the one or more potential abnormalities comprises analyzing each of the one or more corresponding image frame with machine learning algorithms to detect the presence of the one or more potential abnormalities.

18. The method of claim 11, wherein presenting on the display screen the overlay comprises presenting graphical or textual indicia indicating the presence of the one or more potential abnormalities.

19. The method of claim 11, further comprising, with the computer, creating an annotated overlay corresponding to the overlay including additional graphical or textual information entered by the clinician, and storing the annotated overlay.

20. The method of claim 11, wherein the report includes an annotated overlay for the fetal ultrasound examination.

21. The method of claim 11, wherein the report includes the clinician's observations during the fetal ultrasound examination.

22. The method of claim 21, further comprising, with the computer, sending one or more of at least a portion of the motion video clip or the report to an expert.

23. The method of claim 11, further comprising, with the computer, determining a quality value for the fetal ultrasound examination based on the motion video clip.

* * * * *